| United States Patent [19] | [11] Patent Number: 5,173,419 |
|---|---|
| Harman et al. | [45] Date of Patent: Dec. 22, 1992 |

[54] PURIFIED CHITINASES AND USE THEREOF

[75] Inventors: Gary E. Harman; Roxanne M. Broadway, both of Geneva, N.Y.; Arne Tronsmo, Aas, Norway; Matteo Lorito, Geneva, N.Y.

[73] Assignee: Cornell Research Foundation, Inc., Ithaca, N.Y.

[21] Appl. No.: 716,134

[22] Filed: Jun. 17, 1991

[51] Int. Cl.[5] ............................................. C12N 9/42
[52] U.S. Cl. ................................. 435/209; 424/94.61; 435/183; 514/2; 514/12; 530/350; 530/371; 530/823
[58] Field of Search ...................... 514/12, 2; 530/350, 530/823, 370, 371; 424/94.1, 94.61; 435/223, 183, 209

[56] References Cited

U.S. PATENT DOCUMENTS 4,751,081  6/1988  Suslow et al. .......................... 424/93
4,940,840  7/1990  Suslow et al. .................... 435/172.3

FOREIGN PATENT DOCUMENTS

63/123645  5/1988  Japan.
2-286082  11/1990  Japan.

OTHER PUBLICATIONS

Sivan et al., J. Gen. Microbiol. vol. 135(3) pp. 675–682 (1989) Biosis Abstract.
Sandhu et al., Enzyme Microb. Technol. vol. 11 pp. 21–25 (1989).
Usui et al., Carbohydrate Res., vol. 203 pp. 65–77 (1990).
de Vries et al., J. Gen. Microbiol., vol. 76, pp. 319–330 (1973).
WPI Abstract, Asahi-Seibutsu JP 2286082 published Nov. 26, 1990.
Tronsmo A., Norwegian Journal of Agricultural Sciences 3:157–161 (1989).
Tronsmo A., Phytopathology 79(10), 1153 (1989) entry #143.

*Primary Examiner*—Merrell C. Cashion, Jr.
*Assistant Examiner*—Andrew G. Rozycki

[57] ABSTRACT

Two chitinases from *Trichoderma harzianum* P1 (ATCC 74058) show chitin-containing-fungus- and insect-inhibiting activity. The first is an endochitinase having a molecular weight of 36 kDa and an isoelectric point of 5.3±0.2. The second is an exochitinase having a molecular weight of 36 kDa an an isoelectric point of 4.4±0.2. The chitinases can be applied in contact with chitin-containing fungus or insect as an inhibitor thereof. The chitinases can be applied to plants or to soil around plants which need production from a chitinase-containing pest. The chitinases can also be used to isolate genes coding for them which can be inserted into a genome of a plant needing protection from a chitinase-containing pest or into the genome of a microorganism to provide transgenic microorganism useful to produce enzyme or as a biocontrol agent.

3 Claims, 3 Drawing Sheets

PURIFIED CHITINASES AND USE THEREOF

This invention was made in part with Government support under U.S.-Israel Binational Agricultural Research and Development Fund (BARD) grant number US-1723-89. The Government has certain rights in the invention.

TECHNICAL FIELD

This invention is directed to isolation of chitinases for biological control of chitin-containing fungi and insects.

BACKGROUND OF THE INVENTION

Application of broad-spectrum pesticides is the primary method used for controlling fungal and insect pests. Such application has resulted in significant environmental pollution and ecological disruption. Pesticide residues are found in food and groundwater and often eliminate beneficial organisms resulting in emergence of secondary pests. Furthermore, as the target pests become less susceptible to the pesticide, there can be a resurgence of the original pest, requiring application of excessive quantities of pesticides for control.

A number of strategies for biological or biorational control of fungal and insect pests have been envisioned. Among the more attractive strategies are those that target an attribute that is pest specific. One target that has been selected is the structural polymer chitin, which is present in insects and some fungi that attack plants, but is absent in higher plants and vertebrates. U.S. Pat. No. 4,751,081 follows this approach and is directed to novel chitinase-producing bacteria strains for use for inhibiting chitinase-sensitive plant pathogens (fungi and nematodes). The approach of U.S. Pat. No. 4,751,081 lacks flexibility.

SUMMARY OF THE INVENTION

An object of the invention herein is to provide purified chitinases which can be used per se to inhibit fungi and insects that contain chitin or can be used to provide novel chitinase-producing bacteria as in U.S. Pat. No. 4,751,081 or can be used to isolate genes coding for them which can be inserted into a genome of a plant needing protection from a chitin-containing pest.

The chitinases that are the subject of the instant invention are isolated from *Trichoderma harzianum* strain P1 (also designated *Trichoderma harzianium* 107 P1). This strain was deposited with the American Type Culture Collection, 12301 Parklawn Drive, Rockville, Md. 20852 on May 20, 1991, under the terms of the Budapest Treaty, and has been assigned accession number ATCC 74058.

Both of the chitinases herein are essentially pure proteins that inhibit chitin-containing fungi and insects. One has endochitinase activity and has a molecular weight of 36 kDa (as determined by sodium dodecyl sulfate polyacrylamide gel electrophoresis under reducing conditions) and an isoelectric point of $5.3 \pm 0.2$. The other has exochitinase activity and has a molecular weight of 36 kDa (as determined by sodium dodecyl sulfate polyacrylamide gel electrophoresis under reducing conditions) and an isoelectric point of $4.4 \pm 0.2$. These chitinases are sometimes referred to hereinafter as the "purified chitinases herein" or as chitinases "of the invention herein".

The term "essentially pure" is used herein to mean the presence of a single protein band on a sodium dodecyl sulfate polyacrylamide gel submitted to electrophoresis under reducing conditions and stained with silver stain.

The term "inhibit" is used herein to mean reduce the growth and/or development of fungi or insects compared to where inhibiting agent is not present.

The term "endochitinase activity" is used herein to mean ability to cleave chitin randomly. Such activity is readily determined by an assay to measure reduction of turbidity of a suspension of purified chitin by an agent wherein reduction of turbidity indicates endochitinase activity for the agent. The method of purification of the chitin is described in Vessey, J. C., et al, *Transact. Brit. Mycol. Soc.* 60, 133-143 (1973) and involves grinding and washing crab shell chitin (Sigma Chemical Co.) with distilled water, washing with a mixture containing ethanol:diethyl ether:HCl (50:50:1), bleaching with NaOCl, dissolving in HCl, precipitating by diluting with ice water, and then repeatedly washing with water adjusted to pH 8.5 until the pH of the chitin equals at least 3. The assay involves the following: One g. of purified chitin is suspended in 100 ml 50 mM KHPO$_4$ buffer pH 6.7. To a test tube is added 0.5 ml of this suspension; then 0.5 ml of the test sample is added. The tube is incubated at 37° C. for 24 hours and then diluted with 5 ml water. The optical density of a suspension is determined at 510 nm. The percentage reduction in turbidity is calculated relative to addition of a sample without enzyme.

The term "exochitinase activity" is used herein to mean ability to cleave chitin from one end. Such activity is readily determined by standard assays by release of chromogenic head group from p-nitrophenyl-N-acetyl-$\beta$-D-glucosaminide or p-nitrophenyl-$\beta$-D-N,N'-diacetylchitobiose, which substrates respectively measure for activity of $\beta$-N-acetylglucosaminidase (nagase activity) and N,N'-diacetylchitobiase (biase activity). The assays are the same except for the substrate and involve the following: A substrate solution is formed by dissolving 3 mg of substrate in 10 ml 50 mM KHPO$_4$ buffer pH 6.7. One hundred $\mu$l of a substrate solution is added to a well in a microtiter plate (Corning). Thirty $\mu$l of test solution is added, and incubation is carried out at 50° C. for 15 minutes. Then the reaction is stopped by addition of 50 $\mu$l of 0.4M Na$_2$CO$_3$, and the optical density is read at 410 nm. Enzyme solutions may have to be diluted, since optical density readings should be below 1.0. Activity is calculated as the optical density X the dilution factor.

A further aspect of the invention herein involves inhibiting the germination of a chitin-containing fungus which comprises contacting such fungus with an antifungal effective amount of chitinase of the invention herein. In a preferred use, the fungus is from the genus Fusarium.

DETAILED DESCRIPTION

Figure 1:
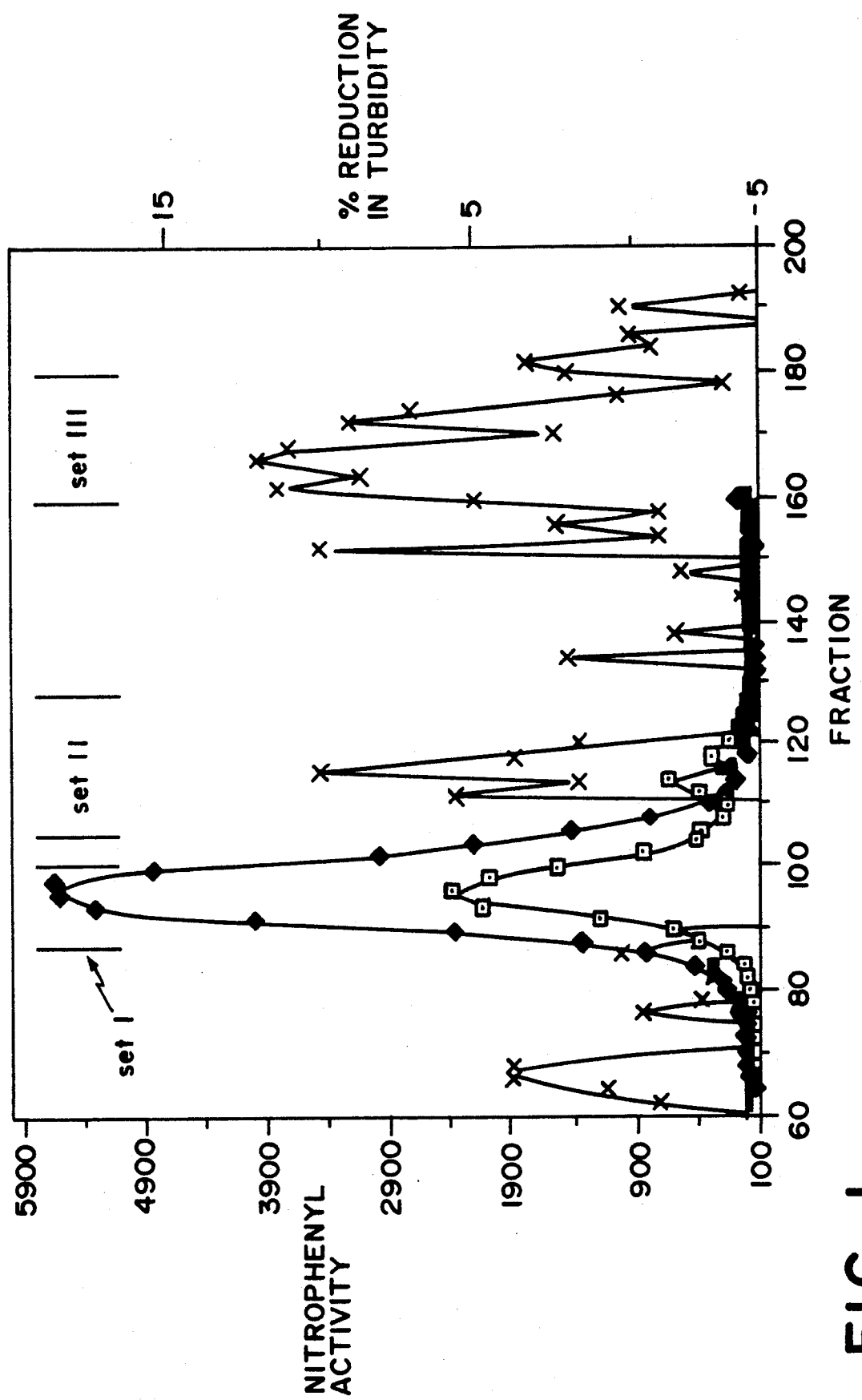
FIG. 1 depicts the elution pattern for the concentrated broth of Example I and provides a graph of endochitinase activity (fraction vs. % reduction in turbidity) denoted by X's, a graph of biase activity (fraction vs. nitrophenyl activity) denoted by open boxes, and a graph of nagase activity (fraction vs. nitrophenyl activity) denoted by filled-in diamonds.

*Trichoderma harzianum* strain P1 (ATCC 74058) arose as a spontaneously occurring isolate on placement of *Trichoderma harzianum* strain 107 on a medium containing 500 ppm of the fungicide iprodione by inventor A. Tronsmo. Strain 107 was isolated from wood shavings by Dr. C. Dennis in Norfolk, England and was selected by Tronsmo and Dennis as a cold tolerant isolate in a survey for biocontrol agents effective in cold climates. *Trichoderma harzianum* strain P1 (ATCC 74058) has been evaluated as a biocontrol agent as described in Tronsmo, A., *Norwegian Journal of Agricultural Sciences*, 3, 157–161, 1989 (biological control of storage rot on carrots) and has been successfully used as a biocontrol agent of *Botrytis cinerea*, a fungus affecting strawberries, grapes and apples. (Unpublished data by Harman, G., et al).

The purified protein chitinases herein are obtained from *Trichoderma harzianum* strain P1 (ATCC 74058) as follows: The strain is readily cultured in modified Richard's medium (composition in one liter of water of 10 g $KNO_3$, 5 g $KH_2PO_4$, 13 g $MgSO_4$, 20 mg $FeCl_3$, 10 g crab shell chitin (Sigma Chemicals), 10 g Polyclar AT (an insoluble polyvinylpyrrolidone from GAF Corp) and 150 ml V8 juice (Campbell Soup Company)) at 25° C. After 3 to 5 days of culturing, the hyphal mass is removed to provide a broth which is dialyzed to remove small molecular weight molecules and then concentrated about 30-fold. The concentrated broth is subjected to liquid chromatography to collect a fraction with biase activity with low nagase activity and a fraction with only endochitinase activity. The fractions are concentrated and the proteins are eluted using a chromatofocusing column. The turbidity reducing portion of the endochitinase activity fraction elutes as a single peak as the essentially pure protein having endochitinase activity, a molecular weight of 36 kDa and an isoelectric point of 5.3±0.2. For the other fraction, the biase portion elutes at a single peak at pH 4.3–4.6 (variation between runs). The biase portion is indicated by polyacrylamide gel electrophoresis under non-reducing conditions to contain three proteins but only the most intensively staining one has biase activity, and it has a molecular weight of 36 kDa and an isoelectric point of 4.4±0.2. The intensively staining protein is isolated from the others by gel filtration liquid chromatography.

The purified chitinases herein inhibit chitin-containing fungi and chitin-containing herbivorous insects. The chitin-containing fungi inhibited by the purified chitinases herein include, for example, species from genera including Fusarium, Gliocladium, Rhizoctonia, Trichoderma, Ustilago, Erysiphe, Botrytis, Sclerotium, and Alternaria. The chitin-containing herbivorous insects inhibited by the purified chitinases herein include, for example, Lepidoptera including *Trichoplusia ni* (cabbage looper), *Pieris rapae* (imported cabbage worm), corn earworm, gypsy moth, pink boll worm, tobacco bollworm, diamondback moth, codling moth and spruce budworm; Coleoptera including Colorado potato beetle, boll weevil, Mexican bean beetle and corn rootworm; Homoptera including citrus psylla, cotton aphid, peach-potato aphid and California red scale; Thysanoptera, including onion thrips; Orthoptera including migratory locusts; Hemiptera including rice stink bug; Diptera including Hessian fly and cabbage root fly; Acari including European red mite, citrus red mite and two spotted mite; Siphonoptera including Lucerne flea; Isoptera including harvester termite; and Hymenoptera including leaf cutting ants.

Inhibition of the aforementioned by the purified chitinases herein is readily carried out by contacting the fungus or insect with the chitinase. A method for inhibiting the germination of a chitin-containing fungus is recited above.

The purified chitinase can be utilized as a solution in a concentration, for example, of 50 ppm to 1000 ppm and applied in the form of a spray, or as a solid wherein purified chitinase is present together with an agriculturally acceptable adhesive carrier, e.g., methyl cellulose or gum arabic, and applied as a powder.

Application can be, for example, to the seed, foliage or roots of a plant to be protected from a chitin-containing insect or plant-pathogenic fungus, or the soil surrounding said plant, or to a chitin-containing fungus or insect to be inhibited.

The purified chitinases herein can also be used to isolate genes coding for them. This can be carried out as follows:

Lyophillized mycelium obtained from *Trichoderma harzianum* P1 (ATCC 74058) is ground into a fine powder and suspended in a lysis buffer. The suspension is treated with oligo dT cellulose resin which absorbs mRNA, which has a polyadenylated (poly $A^{30}$) sequence at the 3' end. Unbound cellular debris, including chromatin DNA, ribosomal RNA, membranes and other molecules are removed by washing the resin. The mRNA is eluted with a low salt buffer and recovered by ethanol precipitation. This procedure yields 20–100 $\mu g$ of poly $A^{30}$ mRNA per gram of dried mycelium. An mRNA isolation kit is commercially available (e.g. from Invitrogen of San Diego, Calif.) for this procedure.

Oligo dT primers are added to 10 $\mu g$ poly $A^{30}$ mRNA with the first cDNA strand synthesized by adding reverse transcriptase and dNTP's. The mRNA is degraded from the mRNA:cDNA hybrid and the second cDNA strand is synthesized by adding dNTP's, DNA polymerase 1, T4 polymerase and *E. coli* ligase. Linkers are added to the newly synthesized cDNA molecules and the molecules are ligated into a viral expression vector to form viral particles containing a cDNA library. Insertion of the linkered cDNA is upstream of the $\beta$-galactosidase stop codon. This formation of viral particles containing a cDNA library from the isolated poly $A^{30}$ mRNA is readily carried out utilizing a commercially available kit (e.g. from Invitrogen). The viral particles express the cDNA coding sequence when placed into *E. coli*.

*E. coli*, strain Y1089, is lytically infected with the viral particles. At the appropriate time, the plaque lawn plate is overlain with a coated membrane that stimulates expression of the $\beta$-galactosidase gene containing the ligated cDNA molecule. Expressed fusion particles bind to the membrane, which is probed with polyclonal antibodies specific for the chitinase of interest. Detection of those plaques expressing the genes of interest is determined using a colony screening system. Those plaques expressing the genes of interest are isolated.

The polyclonal antibodies used above are formed by injecting 300 μg of purified chitinase weekly into a rabbit, for a total of six injections. Total antibodies are isolated from the rabbit serum (Goding, J. W., *Monoclonal Antibodies*, Academic Press, London, 1983), with cross-reactivity and specificity determined using Western blots (Burnett, W. N., *Anal. Biochem.*, 112, 195-203 (1981).

The genes produced as above can be inserted into microorganisms by known methods, e.g. as in U.S. Pat. No. 4,751,081. The transgenic microorganisms can be used to produce chitinase or as biocontrol agents.

The genes produced as above can be also inserted by known methods into plants (e.g. as described in European patent application 339,009) as a defense against chitinase-sensitive pests.

The invention is illustrated in the following specific examples:

EXAMPLE I

Modified Richard's medium (as described hereinbefore) containing 1% chitin from crab shells as the sole carbon source is placed in ten 250 ml Erlenmeyer flasks (100 ml/flask) and sterilization is carried out by autoclaving. Two ml of a heavy suspension of conidia (approximately $10^9$/ml) of *Trichoderma harzianium* strain P1 (ATCC 74058) were used to inoculate each flask and the resulting cultures were grown on a rotary shaker for 4 days at 25° C.

After four days of culturing, the hyphal mass was removed from the medium by centrifugation, and the supernatant (800 ml) was dialyzed against 50 mM $KHPO_4$ buffer pH 6.7 (MWCO 8,000) to remove small molecular weight molecules and then concentrated about 30-fold by applying polyethylene glycol (MW 35,000) to the outside of the dialysis tubing, to produce a concentrated broth.

Figure 2:
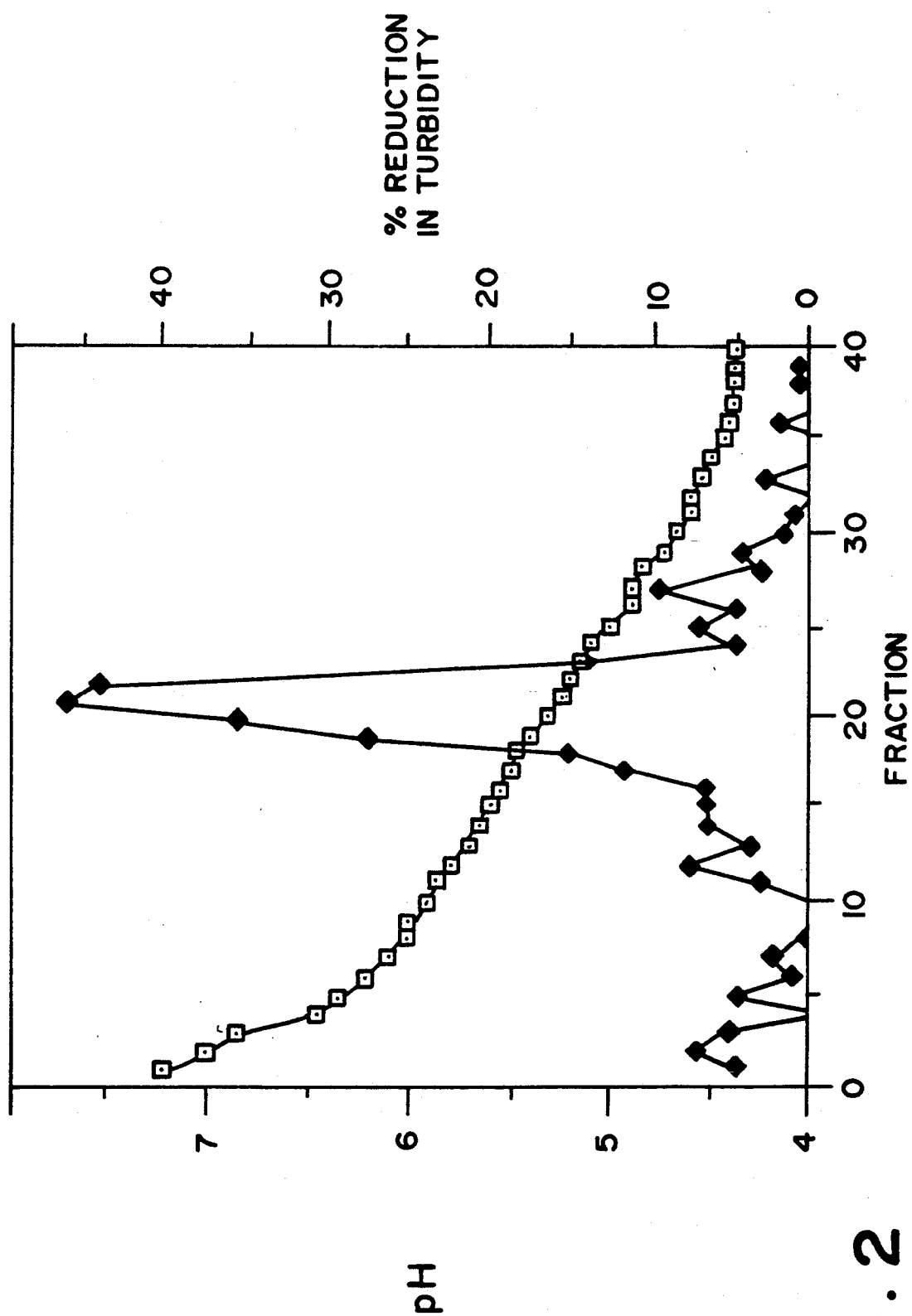
FIG. 2 depicts the elution pattern for concentrated fractions of Sets III of Example I and provides a graph of endochitinase activity (fraction vs. % reduction in turbidity) denoted by filled-in diamonds, and a graph of fraction vs. pH denoted by open boxes.
Figure 3:
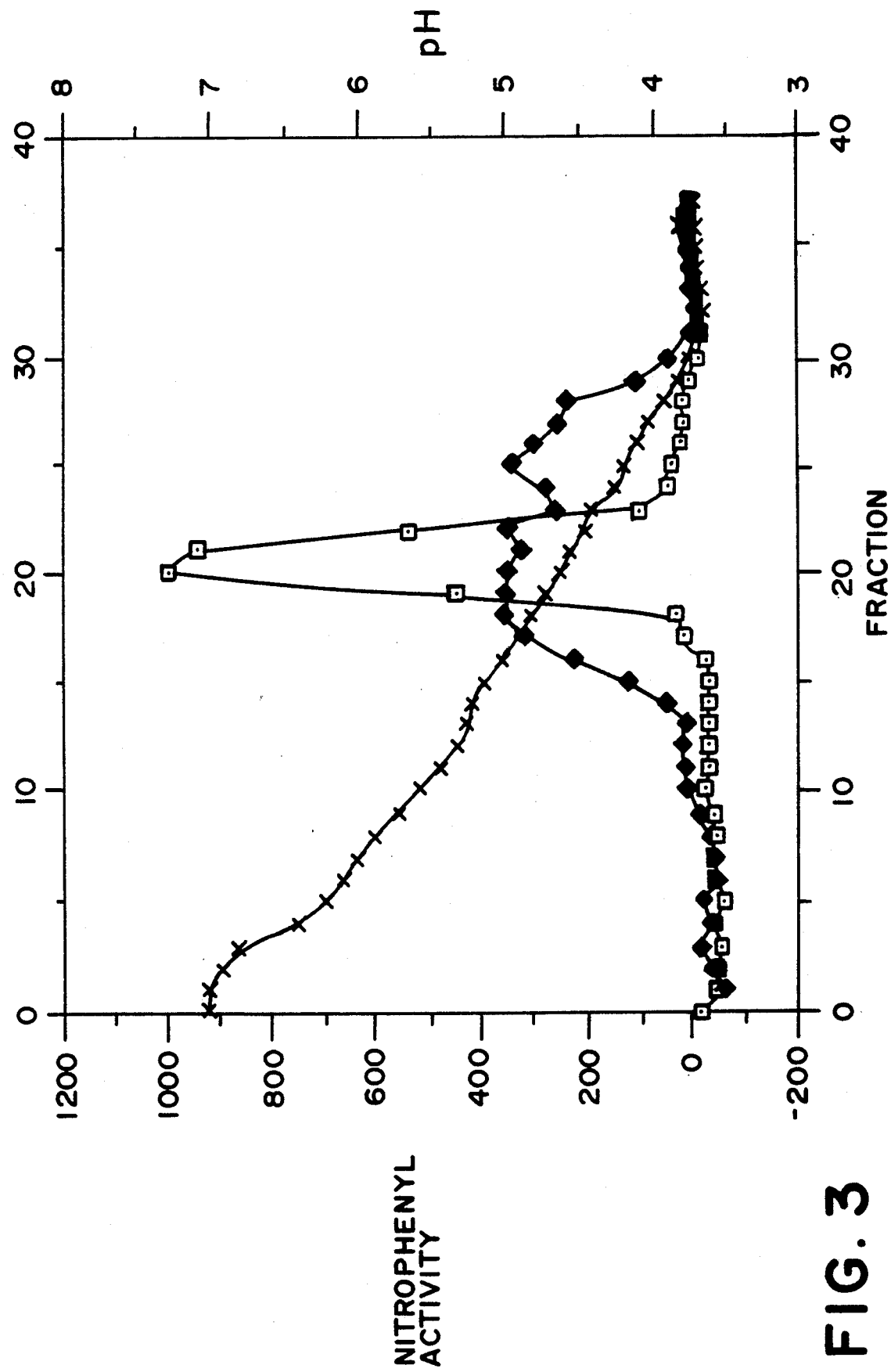
FIG. 3 depicts the elution pattern for concentrated fractions of Sets II of Example I and provides a graph of nagase activity (fraction vs. nitrophenyl activity) denoted by filled-in diamonds, a graph of biase activity (fraction vs. nitrophenyl activity) denoted by a peak at fraction 20 and a graph of fraction vs. pH denoted by a progressively descending path.

The concentrated broth (approximately 30 ml), in two separate samples, was applied to a 5×60 cm Sephacryl S-300 column and eluted with 50 mM $KHPO_4$ buffer pH 6.7 containing 200 mM NaCl. Each elution fraction consisted of about 8 ml. The elution profiles of enzyme activity are shown in FIG. 1. In FIG. 1, the X's denote the graph for % reduction in turbidity (endochitinase activity), the open boxes denote the graph for biase activity and the filled-in diamonds denote the graph for nagase activity. As shown in FIG. 1, the void volume eluted at fraction 60, and a peak of nagase and biase activity eluted at about fraction 100. At about fraction 115 there was a peak of biase activity and endochitinase activity, but little nagase activity. At fractions 160-180 there was a broad peak containing only endochitinase activity. These fractions were combined into three sets, designated I, II and III, as shown on FIG. 1. Set I (approximately 120 ml) contained nagase and biase activity. Set II (approximately 160 ml) contained biase activity and endochitinase activity and a low level of nagase activity. Set III (approximately 200 ml) contained only endochitinase activity. Set II was combined with a similar fraction from another run on the Sephacryl column. Set III was combined with a similar fraction from another run of the Sephacryl column. The Set II combined fractions were dialyzed against 25 mM imidazole-HCl buffer 6.7 and concentrated to 20 to 60 ml. The Set III combined fractions were dialyzed against 25 mM imidazole-HCl buffer 6.7 and concentrated to 20 to 60 ml. These concentrates were applied to 1.1×25 cm chromatofocusing columns equilibrated with 10 mM imidazole buffer. The proteins were eluted with Polybuffer at a pH range of 6.7 to 4. The elution pattern for the concentrate of combined Sets III is shown in FIG. 2 wherein the open boxes denote the graph for pH and the filled-in diamonds denote the graph for % reduction in turbidity. The endochitinase (turbidity reducing) activity from the concentrate of combined Sets III (fraction numbers 20 to 22 consisting of approximately 24 ml) eluted at a single peak at pH $5.3\pm0.2$. The purity of enzyme in this fraction after dialysis and drying was confirmed by polyacrylamide gel electrophoresis under non-denaturing conditions; only a single protein band was detected with silver stain. The protein in this band was determined to have a molecular weight of 36 kDa by sodium dodecyl sulfate polyacrylamide gel electrophoresis under reducing conditions and was determined to have an isoelectric point of $5.3\pm0.2$. The elution pattern for the concentrate of combined Sets II is shown in FIG. 3 wherein the graph denoted by diamonds is for nagase activity, the graph with the peak at about fraction 20 is for biase activity, and the graph that progresses downwardly is for pH. As shown in FIG. 3, the fractions with the greatest amount of biase activity (fractions 19-22 consisting approximately of 32 ml) eluted in a single peak at about pH 4.6. In another run these fractions eluted in a single peak at about pH 4.3. As shown in FIG. 3 these fractions contained some nagase activity. This peak (after diaylsis and drying) was found by polyacrylamide gel electrophoresis under non-reducing conditions to contain three protein bands. Only one of these bands, the most intensively staining one, was found to have biase activity. The protein of this band was determined to have an isoelectric point of $4.4\pm0.2$ and was determined by sodium dodecyl sulfate polyacrylamide gel electrophoresis under reducing conditions to have a molecular weight of about 36 kDa. This protein is isolated from the other two present by gel filtration liquid chromatography on Bio-Gel P-60 (Bio Rad Laboratories).

COMPARATIVE EXAMPLE I

Chitinases isolated from pea, tomato and bean were reported to be endochitinases and to have molecular weights of 27-39 kDa and isoelectric points ranging from 8.87 to 9.4.

An enzyme from *T. reesei* which is an endochitinase was estimated to have a molecular weight of 58 kDa.

The enzyme system of *Serratia marcescens* strain QMB1466 (ATCC 990) was reported to have chitobiase activity. This activity is associated, on sodium dodecyl sulfate polyacrylamide gel electrophoresis under reducing conditions, with two major protein bands of molecular weights at 52.5 and 58 kDa and two minor protein bands of molecular weights of 21.5 and 40.4 kDa. This strain is the one used in the working Example of U.S. Pat. No. 4,751,081 for chitinase activity.

EXAMPLE II

The purified endochitinase from Sets III in Example I (fraction numbers 20 to 22 of FIG. 2) and purified biase enzyme from Sets II in Example I (fraction numbers 19-22 in FIG. 3), that is the fraction containing the essentially pure endochitinase having a molecular weight of 36 kDa and an isoelectric point of $5.3\pm0.2$ (denoted endochitinase below) and the fraction containing the protein having biase activity, a molecular weight of 36 kDa and an isoelectric point of 4.4±0.2 (denoted biase below), were assayed for antifungal activity against *Fusarium sp.* and *Trichoderma harzianum* (ATCC 20847). This was carried out on the dialyzed, dried fractions, as follows: A solution containing 500 ppm of enzyme (dialyzed, dried fraction) in distilled water was prepared and was sterilized by filtration through a 0.45 μm filter. From each sterilized composition an assay mixture was prepared that contained 100 μl of the sterilized composition, 100 μl of 3X potato dextrose broth (Difco Laboratories), and 100 μl of a fungal spore suspension ($10^6$/ml). Each assay mixture was incubated. Results of spore germination after a 12 hour incubation were as follows:

TABLE 1

| Enzyme | Organism | Spore Germination % |
| --- | --- | --- |
| None (control) | Fusarium | 85 |
| Biase | Fusarium | 63 |
| Endochitinase | Fusarium | 58 |
| None (control) | Trichoderma | 49 |
| Biase | Trichoderma | 20 |
| Endochitinase | Trichoderma | 22 |

These data show that spore germination was inhibited by the enzyme solutions.

Other effects were noted as follows: Germ tube growth was inhibited after 24 hours of incubation of the Trichoderma strain by both the biase solution and the endochitinase solution. Among spores producing germ tubes, the average length (of 15 measured) for germ tubes germinating in the absence of the enzyme was 198 μm, while the average length of germ tubes in the presence of the biase was 55 μm and the average length of germ tubes in the presence of the endochitinase was 58 μm.

EXAMPLE III

Filter sterilized broth prepared from *Trichoderma harzianum* strain P1 (ATCC 74058) was compared to filter-sterilized broth for *T. virde* 105, *T. koningii* 8, *T. koningii* 417, *T. koningii* VS023, *T. harzianum* 1295-22, and *Gliocladium virens* VS031 as follows: In each case, a diet was made consisting of the following in parts by weight 57 parts *Trichoderma* or *Gliocladium* broth, 11.4 parts wheat germ, 2 parts casein, 1.4 parts agar, 1 part Vitamin Premix (Hoffman-LaRoche #26862), 0.8 parts Wesson Salt Mixture (Bio Serv, Inc.), 0.2 parts sorbic acid, 0.1 parts methyl paraben, and 26 parts distilled water. Larvae of *T. ni* and *P. rapae* were provided with the diet, ad libitum from neonate until the controls reached the ultimate instar, and then all larvae were weighed. Only two of the fungal strains, *G. virens* VS031 and *T. harzianum* P1 (ATCC 74058), reduced the growth of both the larval *T. ni* and *P. rapae* below 60%. The filter-sterilized broth from each of these two strains was dialyzed (MWCO 8,000) to remove small molecular weight molecules and incorporated into the artificial diet as described above. Again, the broth from these two strains significantly reduced the growth of larval *T. ni* and *P. rapae*. The ammonium sulfate precipitable protein in the filter-sterilized, dialyzed broth from both strains was tested for biological activity against larval *T. ni* and *P. rapae* as above. The chitinase activity of the original P1 broth was not precipitated while that of the VS031 broth was. The ammonium sulfate precipitated protein from strain VS031 significantly reduced larval growth while that of strain P1 did not.

Variations in the invention will be obvious to those skilled in the art. Therefore, the invention is defined by the claims.

What is claimed is:

1. An essentially pure chitin-containing fungus and insect-inhibiting protein having endochitinase activity, which is isolated from *Trichoderma harzianum* strain P1 having accession No. ATCC 74058 and which has a molecular weight of 36 kDa as determined by sodium dodecyl sulfate polyacrylamide gel electrophoresis after the protein was prepared under reducing conditions on comparison to migration of protein of known molecular weight and an isoelectric point of 5.3±0.2 as determined based on its elution profile from a chromatofocusing column.

2. A method of inhibiting the germination and subsequent growth of chitin-containing fungus of a genus selected from the group consisting of Fusarium and Trichoderma which comprises contacting such fungus with an antifungal effective amount of the protein of claim 1.

3. The method of claim 2 wherein the fungus is from the genus Fusarium.

* * * * *